(12) United States Patent
Takaoka et al.

(10) Patent No.: US 9,144,458 B2
(45) Date of Patent: Sep. 29, 2015

(54) ABLATION CATHETER WITH BALLOON AND ABLATION CATHETER SYSTEM WITH BALLOON

(75) Inventors: Motoki Takaoka, Otsu (JP); Akinori Matsukuma, Otsu (JP); Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 802 days.

(21) Appl. No.: 13/320,053

(22) PCT Filed: May 18, 2010

(86) PCT No.: PCT/JP2010/058317
§ 371 (c)(1),
(2), (4) Date: Nov. 11, 2011

(87) PCT Pub. No.: WO2010/134503
PCT Pub. Date: Nov. 25, 2010

(65) Prior Publication Data
US 2012/0059368 A1    Mar. 8, 2012

(30) Foreign Application Priority Data

May 21, 2009    (JP) ................................ 2009-122827

(51) Int. Cl.
*A61B 18/14*    (2006.01)
*A61B 18/08*    (2006.01)
(Continued)

(52) U.S. Cl.
CPC ........... *A61B 18/1492* (2013.01); *A61B 18/082* (2013.01); *A61B 18/1233* (2013.01); *A61B 2018/0022* (2013.01); *A61B 2018/00214* (2013.01); *A61B 2018/00351* (2013.01);
(Continued)

(58) Field of Classification Search
CPC ............... A61B 2018/00797; A61B 2018/124; A61B 2018/0022; A61B 18/1492
USPC .......................... 606/27–31, 41; 607/101–102
See application file for complete search history.

(56) References Cited

U.S. PATENT DOCUMENTS 5,168,880 A * 12/1992 Sogawa et al. ................. 607/102
5,562,720 A * 10/1996 Stern et al. ...................... 607/98
(Continued)

FOREIGN PATENT DOCUMENTS

JP    2000185053 A    7/2000
JP    3607231 B2    1/2005
(Continued)

OTHER PUBLICATIONS

International Application Serial No. PCT/JP2010/058317, International Search Report mailed Jun. 22, 2010, 4 pgs.

*Primary Examiner* — George Evanisko
(74) *Attorney, Agent, or Firm* — RatnerPrestia

(57) ABSTRACT

In order to perform balloon ablation and spot ablation by one ablation catheter without exchanging an ablation catheter body at the time of treatment by catheter ablation, an ablation catheter with a balloon is provided with a catheter shaft, a balloon which is mounted to the front end side in the longitudinal direction of the catheter shaft, a lumen which communicates with the balloon from the end face on the back end side in the abovementioned longitudinal direction, an in-balloon electrode and an in-balloon temperature sensor which are disposed in the balloon, and a front end electrode and a front end temperature sensor which are mounted in a front end region including the end face on the front end side in the abovementioned longitudinal direction.

6 Claims, 7 Drawing Sheets

(51) Int. Cl.
  *A61B 18/00*  (2006.01)
  *A61B 18/12*  (2006.01)
  *A61B 18/04*  (2006.01)

(52) U.S. Cl.
  CPC ............... *A61B2018/00702* (2013.01); *A61B 2018/00791* (2013.01); *A61B 2018/00797* (2013.01); *A61B 2018/00875* (2013.01); *A61B 2018/046* (2013.01); *A61B 2018/124* (2013.01)

(56) References Cited

U.S. PATENT DOCUMENTS

| | | | | |
|---|---|---|---|---|
| 5,571,088 | A * | 11/1996 | Lennox et al. | ............ 604/96.01 |
| 9,503,677 | | 11/1996 | Lennox | |
| 2002/0029062 | A1 * | 3/2002 | Satake | ............ 606/194 |
| 2003/0014046 | A1 * | 1/2003 | Edwards et al. | ............ 606/41 |
| 2003/0216722 | A1 | 11/2003 | Swanson | |
| 2004/0054367 | A1 * | 3/2004 | Jimenez et al. | ............ 606/41 |
| 2006/0009758 | A1 | 1/2006 | Edwards | |
| 2007/0149963 | A1 | 6/2007 | Matsukuma | |
| 2007/0149964 | A1 | 6/2007 | Kawabata | |
| 2008/0039790 | A1 * | 2/2008 | Hasebe | ............ 604/113 |

FOREIGN PATENT DOCUMENTS

| | | |
|---|---|---|
| JP | 2006198209 A | 8/2006 |
| JP | 3892438 B2 | 3/2007 |
| JP | 2008508014 A | 3/2008 |
| JP | 2008136545 A | 6/2008 |
| JP | 4151910 B2 | 9/2008 |
| JP | 2008302226 A | 12/2008 |
| WO | WO-2006137184 A1 | 12/2006 |
| WO | WO-2008043074 A2 | 4/2008 |

* cited by examiner

ABLATION CATHETER WITH BALLOON AND ABLATION CATHETER SYSTEM WITH BALLOON

CROSS-REFERENCE TO RELATED APPLICATIONS

This application is the U.S. National Phase application of PCT International Application No. PCT/JP2010/058317, filed May 18, 2010, and claims priority to Japanese Patent Application No. JP2009-122827, filed May 21, 2009, the disclosures of which PCT and priority applications are incorporated herein by reference in their entirely for all purposes.

FIELD OF THE INVENTION

The present invention relates to an ablation catheter with a balloon and an ablation catheter system with a balloon.

BACKGROUND OF THE INVENTION

Catheter ablation is an arrhythmia treatment method of inserting an ablation catheter into a cardiac chamber and applying heat between an electrode at a tip portion of the catheter and a counter electrode plate to ablate a myocardial tissue. The catheter ablation is conducted mainly for treatment of tachyarrhythmias such as a paroxysmal supraventricular tachycardia, an atrial tachycardia, an atrial flutter, and a paroxysmal ventricular tachycardia and is a technique of diagnosing a pathogenetic mechanism and a trigger region of an arrhythmia in a cardiac electrophysiological study, thereafter making an electrode of an ablation catheter reach the trigger region of the arrhythmia from the interior of a cardiac chamber, and repeating an operation of applying the electrode to a causative myocardial tissue in the region and heating the tissue at 50 to 65° C. for approximately 60 seconds.

Many of the ablation catheters currently in use have a metallic electrode at a tip portion of the catheter, and each of such catheters generally adopts a technique of bringing the metallic electrode into contact with a myocardial tissue in a dotted manner and forming an ablation line while moving the electrode little by little to isolate the trigger region of the arrhythmia (Patent Literature 1).

However, the ablation catheter having the metallic electrode requires several dozen times of repeated ablations to form the ablation line and isolate the trigger region of the arrhythmia and thus causes problems of a prolonged operation and a heavy burden imposed on a patient. Also, since the small metallic electrode needs to be brought into contact with the target region of the myocardial tissue accurately to form the ablation line with the ablation catheter, a physician requires an advanced technique to manipulate the ablation catheter. Further, since the myocardial tissue is ablated in the dotted manner, an insufficient ablation line with spaces between the ablated regions may be formed, in which case the trigger region of the arrhythmia cannot be isolated completely, which may cause recurrence of the arrhythmia.

To solve the above problems, an ablation catheter with a balloon having a balloon at the tip portion of a catheter shaft has been developed recently, and an ablation catheter system with a balloon including a radio-frequency generator and a balloon surface temperature uniforming device has been reported (Patent Literature 2 and 3).

The ablation catheter system with a balloon is a system of inflating a balloon fixed to the tip side of a catheter shaft by a liquid for heating and heating the liquid for heating by a radio-frequency current supplied from a radio-frequency generator to ablate the entire myocardial tissue contacting the surface of the balloon (hereinafter referred to as balloon ablation).

PATENT LITERATURE

Patent Literature 1: Japanese Patent No. 4151910
Patent Literature 2: Japanese Patent No. 3607231
Patent Literature 3: Japanese Patent No. 3892438

SUMMARY OF THE INVENTION

It has been discovered that the trigger region of the arrhythmia cannot be isolated completely even with use of the ablation catheter system with a balloon in many cases. For a region that the balloon cannot reach, additional dotted ablation (hereinafter referred to as spot ablation) needs to be conducted with use of an ablation catheter having a metallic electrode under present circumstances. In this case, after the ablation catheter with a balloon is removed from the patient, the ablation catheter having a metallic electrode prepared in advance needs to be inserted in the cardiac chamber separately, which imposes a heavy burden on the physician and the patient due to a prolonged operation.

The present invention makes it possible to conduct balloon ablation and spot ablation with a single ablation catheter without replacement of an ablation catheter main body in a treatment by catheter ablation.

As a result of concerted study, the present inventors arrived at the following invention upon successfully making an ablation catheter with a balloon having a spot ablation function.

According to one aspect, the present invention provides an ablation catheter with a balloon including a catheter shaft, a balloon fixed to a front side in a longitudinal direction of the catheter shaft, a lumen communicating with the balloon from an end section on a rear side in the longitudinal direction, an in-balloon electrode and an in-balloon temperature sensor arranged in an interior of the balloon, and a front portion electrode and a front portion temperature sensor attached to a front area containing an end section on the front side in the longitudinal direction.

The above ablation catheter with a balloon can conduct balloon ablation and spot ablation without replacement of an ablation catheter main body.

A distance from the end section on the front side in the longitudinal direction of the catheter shaft to a front end of the front portion electrode in the longitudinal direction is preferably 4 to 10 mm.

When the distance from the end section on the front side in the longitudinal direction of the catheter shaft to the front end of the front portion electrode in the longitudinal direction is 4 to 10 mm, it is possible to prevent unintended abnormal heat generation of a tissue or blood brought into contact with the front portion electrode at the time of balloon ablation.

Also, the present invention provides an ablation catheter system with a balloon including the above ablation catheter with a balloon and a circuit switching switch switching between a first balloon heating circuit (a) described below and a front end heating circuit (b) described below, and this ablation catheter system with a balloon preferably includes an impedance measuring device measuring impedance of the first balloon heating circuit or the front end heating circuit:

(a) a first balloon heating circuit having the in-balloon electrode, a counter electrode, the in-balloon temperature sensor, and a radio-frequency generator; and (b) a front end heating circuit having the front portion electrode, the counter electrode, the front portion temperature sensor, and the radio-frequency generator.

With the above ablation catheter system with a balloon, a surface temperature of the balloon during balloon ablation can be kept to a target temperature uniformly, and balloon ablation and spot ablation can be switched selectively by the circuit switching switch.

Also, by measuring the impedance of the first balloon heating circuit, an impedance change in a case where damage such as a pinhole is generated in the balloon can be detected easily. Consequently, a treatment by the ablation catheter with a balloon in which the damage has been generated can be interrupted, and the catheter can be replaced immediately, which can reduce a burden on a patient. Also, by measuring the impedance of the front end heating circuit, appropriate treatment end timing for an ablated region can be determined, which can prevent excessive ablation and generation of a complication.

Also, the two in-balloon electrodes are preferably arranged.

When the two in-balloon electrodes are arranged, radio-frequency currents flow only in the interior of the balloon and do not flow in the front portion electrode. Thus, regardless of the distance from the end section on the front side in the longitudinal direction of the catheter shaft to the front end of the front portion electrode in the longitudinal direction, unintended abnormal heat generation of a tissue or blood brought into contact with the front portion electrode can be prevented at the time of balloon ablation.

Also, the present invention provides an ablation catheter system with a balloon including the above ablation catheter with a balloon in which the two in-balloon electrodes are arranged and a circuit switching switch switching between a front end heating circuit (b) described below and a second balloon heating circuit (c) described below, and this ablation catheter system with a balloon preferably includes an impedance measuring device measuring impedance of the front end heating circuit:

(b) a front end heating circuit having the front portion electrode, a counter electrode, the front portion temperature sensor, and a radio-frequency generator; and (c) a second balloon heating circuit having the in-balloon electrodes, the in-balloon temperature sensor, and the radio-frequency generator.

With the above ablation catheter system with a balloon, the surface temperature of the balloon during balloon ablation can be kept to a target temperature uniformly, and balloon ablation and spot ablation can be switched selectively by the circuit switching switch.

Also, by measuring the impedance of the front end heating circuit, appropriate treatment end timing for an ablated region can be determined, which can prevent excessive ablation and generation of a complication.

The above ablation catheter system with a balloon preferably includes the radio-frequency generator making radio-frequency currents flow between the in-balloon electrode and the counter electrode and between the in-balloon electrodes or between the front portion electrode and the counter electrode, and a vibration imparting device imparting a vibration to a liquid for heating by periodically repeating suction and ejection of the liquid for heating from the lumen. The vibration imparting device preferably includes a pump selected from the group consisting of a roller pump, a diaphragm pump, a bellows pump, a vane pump, a centrifugal pump, and a pump constituted by combination of a piston and a cylinder.

With the above pump, a vibration to periodically repeat suction and ejection can be imparted to the liquid for heating filled in the lumen and the interior of the balloon, and thus the surface temperature of the balloon can be kept uniform more effectively.

With the present invention, after a tissue is ablated over a wide range with a balloon surface heated uniformly, spot ablation can be conducted partially with a front portion electrode of an ablation catheter system with a balloon without replacement of a catheter main body, which can achieve significant shortening of operation time and accompanying significant reduction of a burden on a patient. Also, with the present invention, it is possible to prevent unintended abnormal heat generation of a tissue or blood brought into contact with the front portion electrode during balloon ablation in which radio-frequency currents flow in a balloon heating circuit, which can prevent a serious complication such as thromboembolism, pulmonary vein stenosis, or esophageal perforation and achieve improvement in safety of ablation.

DETAILED DESCRIPTION OF THE INVENTION

Figure 1:
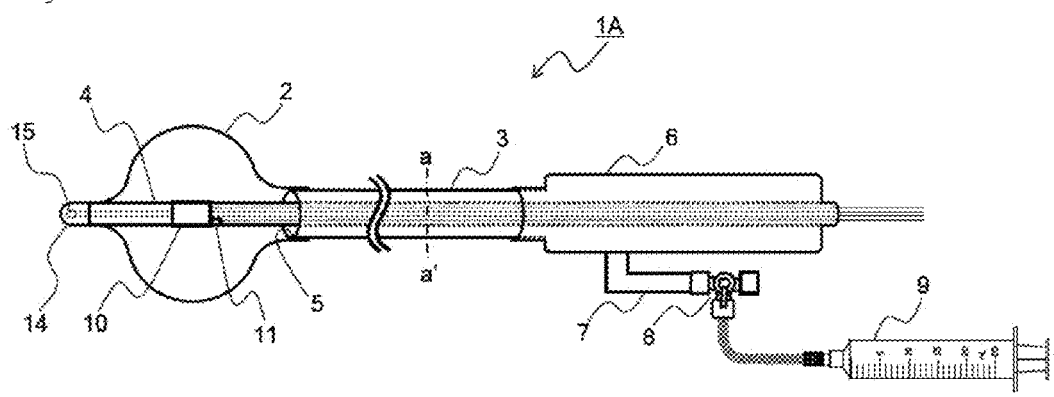
FIG. 1 is a schematic view illustrating an ablation catheter with a balloon according to a first embodiment of the present invention.

Preferred embodiments of the present invention will be described below with reference to the accompanying drawings, but the present invention is not limited to these embodiments. Like reference characters denote similar or identical parts throughout the several views thereof, and duplicate explanation is omitted. Also, the ratio in the drawings does not necessarily correspond to an actual ratio.

An ablation catheter with a balloon according to embodiments of the present invention includes a catheter shaft, a balloon fixed to a front side in a longitudinal direction of the catheter shaft, a lumen communicating with the balloon from an end section on a rear side in the longitudinal direction, an in-balloon electrode and an in-balloon temperature sensor arranged in an interior of the balloon, and a front portion electrode and a front portion temperature sensor attached to a front area containing an end section on the front side in the longitudinal direction.

Figure 2:
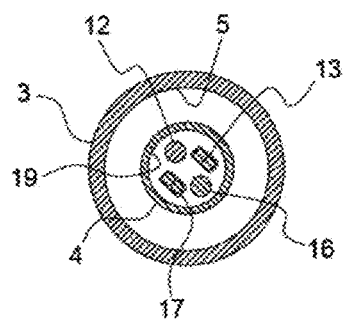
FIG. 2 is a schematic cross-sectional view along the line a-a' of a catheter shaft used in the ablation catheter with a balloon in FIG. 1.

FIG. 1 is a schematic view illustrating an ablation catheter with a balloon according to a first embodiment of the present invention. FIG. 2 is a schematic cross-sectional view along the line a-a' of a catheter shaft used in the ablation catheter with a balloon in FIG. 1.

An ablation catheter with a balloon 1A shown in FIG. 1 has a double-cylinder catheter shaft in which an inner catheter shaft 4 is inserted into a lumen A 5 passing through an outer catheter shaft 3 in a longitudinal direction, and on a front side in the longitudinal direction of the double-cylinder catheter shaft is attached to a balloon 2 that can inflate and deflate. A front portion of the balloon 2 is fixed to a front portion in the longitudinal direction of the inner catheter shaft 4 while a rear portion of the balloon 2 is fixed to a front portion in the longitudinal direction of the outer catheter shaft 3, and a space between the outer catheter shaft 3 and the inner catheter shaft 4 communicates with an interior of the balloon 2.

A rear portion in the longitudinal direction of the inner catheter shaft 4 is fixed in an interior of a handle 6, and the space between the outer catheter shaft 3 and the inner catheter shaft 4 communicates with a three-way stopcock 8 and a syringe 9 via the interior of the handle 6 and a side port 7.

An in-balloon electrode 10 is attached to the inner catheter shaft 4 in the interior of the balloon 2 while an in-balloon temperature sensor 11 is attached to a rear end of the in-balloon electrode 10. An in-balloon electrode lead wire 12 connected to the in-balloon electrode 10 and an in-balloon temperature sensor lead wire 13 connected to the in-balloon temperature sensor 11 are inserted into interiors of a lumen B 19 passing through the inner catheter shaft 4 in the longitudinal direction and the handle 6.

A front portion electrode 14 is attached to a front area of the inner catheter shaft 4 at an exterior of the balloon 2 while a front portion temperature sensor 15 is attached so as to be buried in an interior of the front portion electrode 14. A front portion electrode lead wire 16 connected to the front portion electrode 14 and a front portion temperature sensor lead wire 17 connected to the front portion temperature sensor 15 are inserted into the interiors of the lumen B 19 of the inner catheter shaft 4 and the handle 6.

A material for the balloon 2 is preferably a stretchable material with excellent antithrombogenicity and is more preferably a polyurethane polymeric material.

Examples of the polyurethane polymeric material include thermoplastic polyether urethane, polyether polyurethane urea, fluorine polyether urethane urea, a polyether polyurethane urea resin, and polyether polyurethane urea amide.

From a viewpoint of enabling the balloon 2 to closely contact a trigger region of an arrhythmia, the diameter of the balloon 2 is preferably 20 to 40 mm, the shape is preferably a spherical shape, and the film thickness is preferably 20 to 100 µm.

Each length of the outer catheter shaft 3 and the inner catheter shaft 4 is preferably 0.5 to 2 m from a viewpoint of making the balloon 2 reach a myocardial tissue.

Each diameter of the outer catheter shaft 3 and the inner catheter shaft 4 is preferably 2 to 5 mm from a viewpoint of inserting each of them into a blood vessel.

Each material for the outer catheter shaft 3 and the inner catheter shaft 4 is preferably a flexible material with excellent antithrombogenicity such as a fluorine resin, a polyamide resin, a polyurethane resin, or a polyimide resin.

The cross-sectional area of the lumen A 5 in a cross-section perpendicular to a direction of a long axis of the outer catheter shaft 3 is preferably 3 to 12 mm$^2$ from a viewpoint of enabling to supply a liquid for heating smoothly from the three-way stopcock 8 with use of the syringe 9. The inner diameter of the lumen A 5 is preferably 2 to 4 mm when the lumen A 5 is cylindrical as shown in FIG. 2.

Examples of a method for attaching the in-balloon electrode 10 to the inner catheter shaft 4 include caulking, adhesion, welding, and a heat shrinkable tube.

The shape of the in-balloon electrode 10 is preferably a tubular shape with a length of 5 to 20 mm. From a viewpoint of improving flexibility in a range in which the in-balloon electrode 10 is fixed, the shape of the in-balloon electrode 10 is more preferably a coiled shape, or the in-balloon electrode 10 is more preferably divided into plural pieces.

Each diameter of an electric wire of the coiled in-balloon electrode 10, the in-balloon electrode lead wire 12, and the front portion electrode lead wire 16 is preferably 0.1 to 1 mm.

Examples of each material for the in-balloon electrode 10 and the front portion electrode 14 include gold, silver, platinum, copper, and an alloy of these metals.

Examples of each material for the in-balloon electrode lead wire 12 and the front portion electrode lead wire 16 include copper, silver, gold, platinum, tungsten, and an alloy of these metals, and each of the in-balloon electrode lead wire 12 and the front portion electrode lead wire 16 is preferably provided with an electrical insulating protective coat such as a fluorine resin from a viewpoint of preventing short circuit.

The in-balloon temperature sensor 11 is preferably fixed to the in-balloon electrode 10 or the inner catheter shaft 4 from a viewpoint of measuring a temperature of the interior of the balloon 2 in a stable manner but may be fixed to an inner surface of the balloon 2 from a viewpoint of measuring a surface temperature of the balloon 2.

Examples of the in-balloon temperature sensor 11 and the front portion temperature sensor 15 include a thermocouple and a resistance-temperature detector.

Each diameter of the in-balloon temperature sensor lead wire 13 and the front portion temperature sensor lead wire 17 is preferably 0.05 to 0.5 mm.

Examples of each material for the in-balloon temperature sensor lead wire 13 and the front portion temperature sensor lead wire 17 include copper, silver, gold, platinum, tungsten, and an alloy of these metals when the in-balloon temperature sensor 11 is a resistance-temperature detector, and each of the in-balloon temperature sensor lead wire 13 and the front portion temperature sensor lead wire 17 is preferably provided with an electrical insulating protective coat such as a fluorine resin from a viewpoint of preventing short circuit. Also, when the in-balloon temperature sensor 11 is a thermocouple, each material for the in-balloon temperature sensor lead wire 13 and the front portion temperature sensor lead wire 17 is preferably the same material as that for the thermocouple, and examples of the material include copper and constantan when the in-balloon temperature sensor 11 is a Type T thermocouple while examples of the material include chromel and alumel when the in-balloon temperature sensor 11 is a Type K thermocouple.

Examples of a method for attaching the front portion electrode 14 to the inner catheter shaft 4 include caulking, adhesion, welding, and press fitting.

The distance from an end section on the front side in the longitudinal direction of the inner catheter shaft 4 to a front end of the front portion electrode 14 in the longitudinal direction is preferably 4 mm or longer and is more preferably 4 to 10 mm from a viewpoint of preventing unintended abnormal heat generation of a tissue or blood brought into contact with the front portion electrode 14 at the time of balloon ablation.

The shape of the front end of the front portion electrode 14 is preferably semispherical from a viewpoint of preventing a damage of a contacted tissue.

The front portion temperature sensor 15 is preferably attached so as to be buried in the interior of the front portion electrode 14 from a viewpoint of measuring a neighbor temperature of the front portion electrode 14 in a stable manner.

The liquid for heating is preferably a contrast medium or a contrast medium diluted with saline from a viewpoint of enabling the inflated balloon 2 to be confirmed on an X-ray fluoroscopic image. Meanwhile, in a case where the in-balloon electrode 10 is to be supplied with radio-frequency currents, the liquid for heating is preferably an ionic contrast medium or a contrast medium diluted with saline from a viewpoint of being conductive.

Also, an ablation catheter system with a balloon according to embodiments of the present invention includes a circuit switching switch switching between (a) a first balloon heating circuit having the in-balloon electrode, a counter electrode, the in-balloon temperature sensor, and a radio-frequency generator and (b) a front end heating circuit having the front portion electrode, the counter electrode, the front portion temperature sensor, and the radio-frequency generator.

Figure 3:
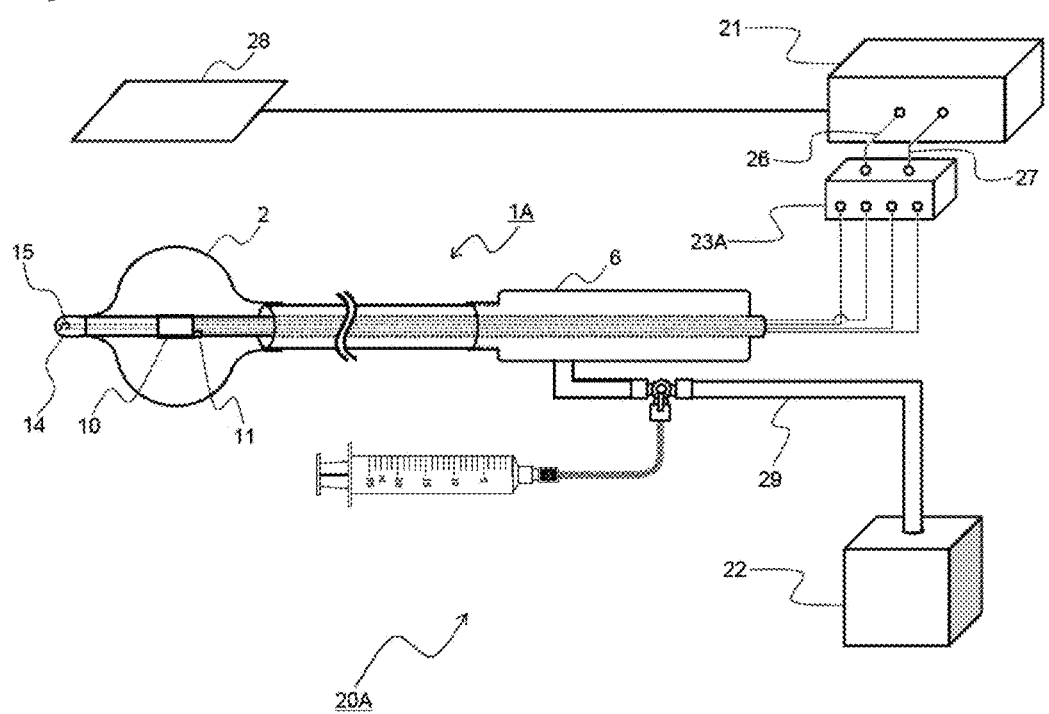
FIG. 3 is a schematic view illustrating an ablation catheter system with a balloon according to the first embodiment of the present invention.
Figure 4:
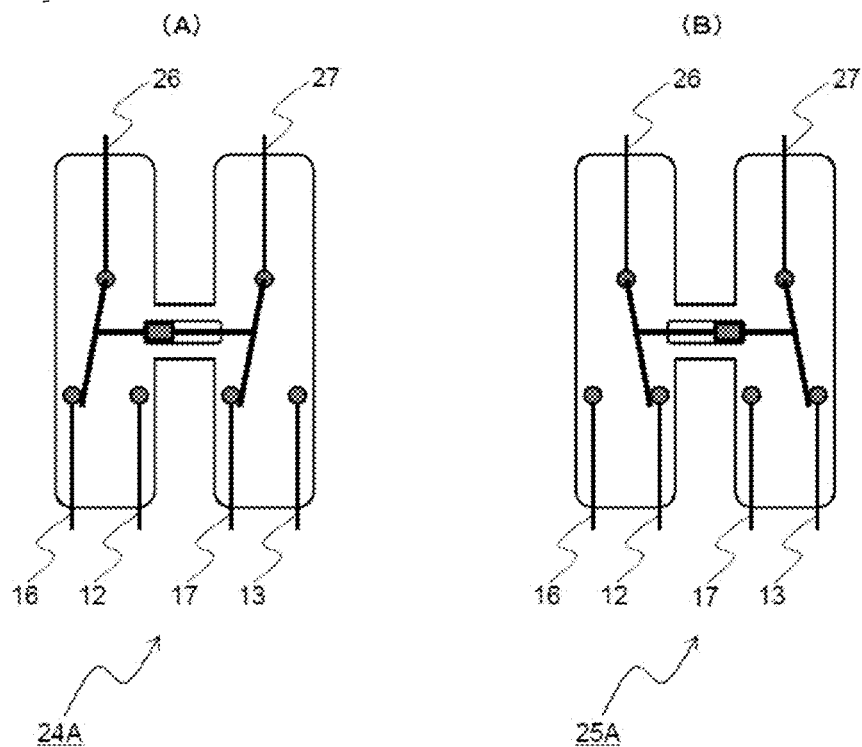
FIG. 4 is a schematic view illustrating a circuit switching switch of the ablation catheter system with a balloon according to the first embodiment of the present invention.

FIG. 3 is a schematic view illustrating an ablation catheter system with a balloon according to the first embodiment of the present invention. Also, 4 is a schematic view illustrating a circuit switching switch of the ablation catheter system with a balloon according to the first embodiment of the present invention.

An ablation catheter system with a balloon 20A is roughly constituted by the ablation catheter with a balloon 1A, a radio-frequency generator 21, and a vibration imparting device 22.

The in-balloon electrode lead wire 12, the in-balloon temperature sensor lead wire 13, the front portion electrode lead wire 16, and the front portion temperature sensor lead wire 17 inserted into the interiors of the lumen B 19 of the inner catheter shaft 4 and the handle 6 are connected to a circuit switching switch 23A.

The other ends of a radio-frequency current lead wire 26 and a temperature measuring signal transmitting lead wire 27 connected to the circuit switching switch 23A that can switch between a front end heating circuit 24A and a first balloon heating circuit 25A are connected to the radio-frequency generator 21. The other end of a lead wire connected to a counter electrode 28 to be applied to a surface of a patient's body is also connected to the radio-frequency generator 21.

To the front end heating circuit 24A are connected the front portion electrode lead wire 16, the radio-frequency current lead wire 26, the front portion temperature sensor lead wire 17, and the temperature measuring signal transmitting lead wire 27. When radio-frequency currents flow between the counter electrode 28 and the front portion electrode 14, spot ablation by the front portion electrode 14 is enabled.

During the spot ablation, a temperature control unit in the radio-frequency generator 21 automatically controls an output of the radio-frequency currents based on a temperature measuring signal of the front portion temperature sensor 15.

To the first balloon heating circuit 25A are connected the in-balloon electrode lead wire 12, the radio-frequency current lead wire 26, the in-balloon temperature sensor lead wire 13, and the temperature measuring signal transmitting lead wire 27. When radio-frequency currents flow between the counter electrode 28 and the in-balloon electrode 10, balloon ablation by the balloon 2 is enabled.

During the balloon ablation, the temperature control unit in the radio-frequency generator 21 automatically controls the output of the radio-frequency currents based on a temperature measuring signal of the in-balloon temperature sensor 11.

The frequency of the radio-frequency currents of the radio-frequency generator 21 is preferably 100 kHz or higher from a viewpoint of preventing an electric shock of a patient and is more preferably 1 to 5 MHz from a viewpoint of efficient current conduction both in the front end heating circuit 24A and in the first balloon heating circuit 25A.

The ablation catheter system with a balloon according to the first embodiment of the present invention preferably has an impedance measuring device measuring impedance of the first balloon heating circuit or the front end heating circuit.

The impedance measuring device is preferably arranged in an interior of the radio-frequency generator 21 and can preferably control automatically or interrupt the output of the radio-frequency currents in accordance with a measurement value of the impedance.

During the spot ablation, the impedance measuring device measures the sum of impedance of a device circuit from the counter electrode 28 to the front portion electrode 14 and a body tissue between the counter electrode 28 and the front portion electrode 14 and can end the spot ablation at appropriate timing based on an impedance change of the body tissue caused by tissue necrosis or the like.

During the balloon ablation, the impedance measuring device measures the sum of impedance of a device circuit from the counter electrode 28 to the in-balloon electrode 10, the liquid for heating sandwiched between the counter electrode 28 and the in-balloon electrode 10, the balloon 2, and a body tissue and can interrupt the balloon ablation immediately based on impedance changes of the liquid for heating and the balloon 2 caused by a pinhole or the like to reduce a burden on a patient.

Also, an ablation catheter system with a balloon in which the two in-balloon electrodes are arranged includes a circuit switching switch switching between (b) a front end heating circuit having the front portion electrode, a counter electrode, the front portion temperature sensor, and a radio-frequency generator and (c) a second balloon heating circuit having the in-balloon electrodes, the in-balloon temperature sensor, and the radio-frequency generator.

Figure 5:
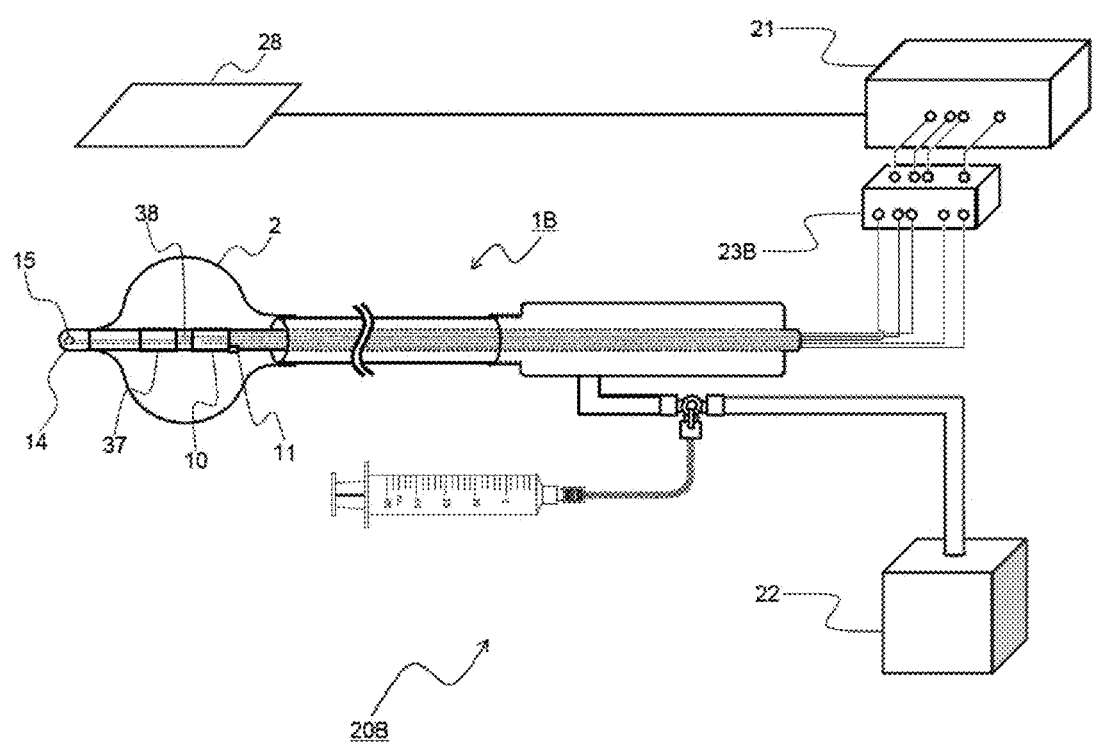
FIG. 5 is a schematic view illustrating an ablation catheter system with a balloon according to a second embodiment of the present invention.
Figure 6:
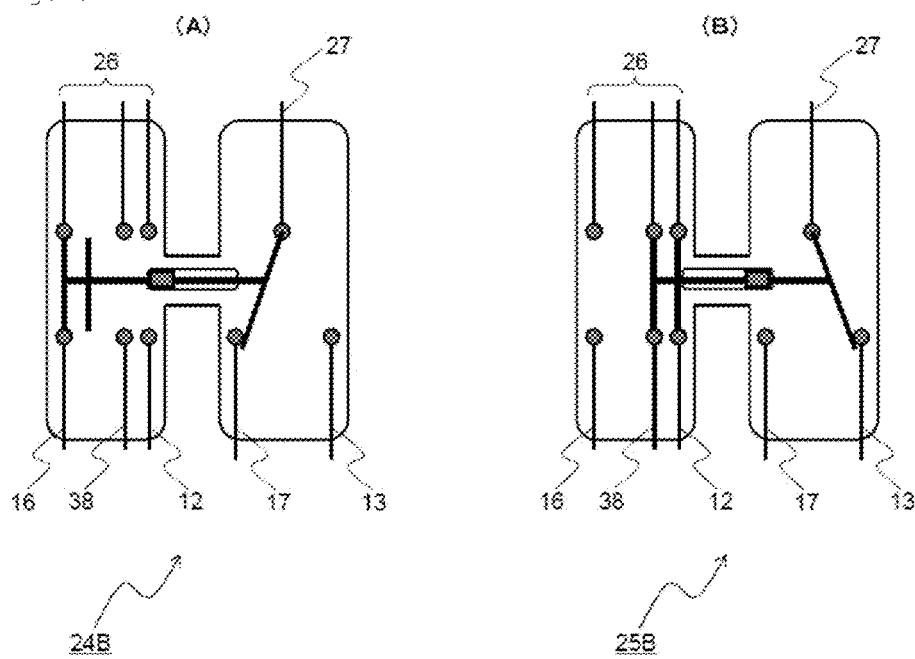
FIG. 6 is a schematic view illustrating a circuit switching switch, as a second embodiment, of the ablation catheter system with a balloon according to the second embodiment of the present invention.

FIG. 5 is a schematic view illustrating an ablation catheter system with a balloon according to a second embodiment of the present invention. Also, 6 is a schematic view illustrating a circuit switching switch of the ablation catheter system with a balloon according to the second embodiment of the present invention.

An ablation catheter system with a balloon 20B is roughly constituted by an ablation catheter with a balloon 1B, the radio-frequency generator 21, and the vibration imparting device 22.

The in-balloon electrode lead wire 12, the in-balloon temperature sensor lead wire 13, the front portion electrode lead wire 16, and the front portion temperature sensor lead wire 17 inserted into the interiors of the lumen B 19 of the inner catheter shaft 4 and the handle 6 are connected to a circuit switching switch 23B. Also, an additional in-balloon electrode lead wire 38 connected to an additional in-balloon electrode 37 attached further on the front side than the in-balloon electrode 10 is inserted into the interiors of the lumen B 19 of the inner catheter shaft 4 and the handle 6 and is connected to the circuit switching switch 23B.

The other ends of the radio-frequency current lead wire 26 and the temperature measuring signal transmitting lead wire 27 connected to the circuit switching switch 23B that can switch between a front end heating circuit 24B and a second balloon heating circuit 25B are connected to the radio-frequency generator 21. The other end of the lead wire connected to the counter electrode 28 to be applied to the surface of the patient's body is also connected to the radio-frequency generator 21.

To the second balloon heating circuit 25B are connected the in-balloon electrode lead wire 12, the additional in-balloon electrode lead wire 38, the radio-frequency current lead wire 26, the in-balloon temperature sensor lead wire 13, and the temperature measuring signal transmitting lead wire 27. When radio-frequency currents flow between the in-balloon electrode 10 and the additional in-balloon electrode 37, balloon ablation by the balloon 2 is enabled. Meanwhile, no radio-frequency currents flow in the counter electrode 28 in this case.

During the balloon ablation, the temperature control unit in the radio-frequency generator 21 automatically controls the output of the radio-frequency currents based on a temperature measuring signal of the in-balloon temperature sensor 11.

Also, with the balloon heating circuit 25B, since the radio-frequency currents flow only between the in-balloon electrode 10 and the additional in-balloon electrode 37, the leakage of the radio-frequency currents into the front portion electrode 14 does not occur at all. Even when the distance from the end section on the front side in the longitudinal direction of the inner catheter shaft 4 to the front end of the front portion electrode 14 in the longitudinal direction is less than 4 mm, unintended abnormal heat generation of a tissue or blood brought into contact with the front portion electrode 14 never occurs.

The ablation catheter system with a balloon according to the second embodiment of the present invention preferably has an impedance measuring device measuring impedance of the front end heating circuit.

The impedance measuring device is preferably arranged in the interior of the radio-frequency generator 21 and can preferably control automatically or interrupt the output of the radio-frequency currents in accordance with a measurement value of the impedance.

During the spot ablation, the impedance measuring device measures the sum of impedance of a device circuit from the counter electrode 28 to the front portion electrode 14 and a body tissue between the counter electrode 28 and the front portion electrode 14 and can end the spot ablation at appropriate timing based on an impedance change of the body tissue caused by tissue necrosis or the like.

Further, the ablation catheter system with a balloon according to embodiments of the present invention includes the radio-frequency generator making radio-frequency currents flow between the in-balloon electrode and the counter electrode and between the in-balloon electrodes or between the front portion electrode and the counter electrode, and a vibration imparting device imparting a vibration to a liquid for heating by periodically repeating suction and ejection of the liquid for heating from the lumen.

Figure 7:
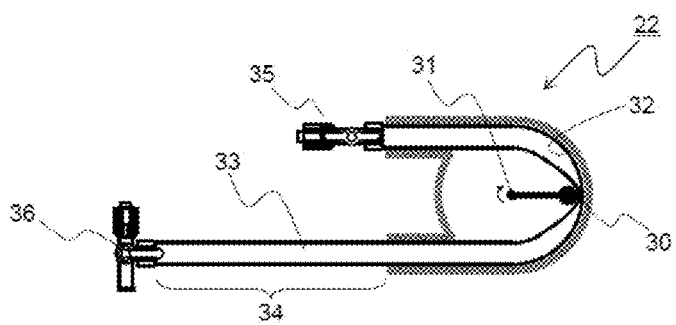
FIG. 7 is a schematic view illustrating an embodiment of a vibration imparting device in the ablation catheter system with a balloon according to the present invention.

FIG. 7 is a schematic view illustrating an embodiment of the vibration imparting device in the ablation catheter with a balloon according to an embodiment of the present invention.

A roller 30 is rotated by a motor around a rotating shaft 31. When the roller 30 is opposed to a guide surface 32, mutually opposing tube walls of an elastic tube 33 closely contact, the elastic tube 33 is closed, and a reservoir portion 34 is pressurized. On the other hand, when the roller 30 is not opposed to the guide surface 32, the elastic tube 33 is expanded to have an original diameter by an elastic restoring effect, the elastic tube 33 is in a communicating state, and the pressure of the reservoir portion 34 is released. In this manner, periodically repeating suction and ejection of the liquid from the reservoir portion 34 toward the balloon 2 by rotation of the roller 30 enables a vibration to be imparted to the liquid for heating. Meanwhile, during the spot ablation, no vibration needs to be imparted to the liquid for heating.

A material for the elastic tube 33 is preferably silicone from a viewpoint of easy elastic restoration.

A pressure-resistant extension tube 29 is preferably a tube made of a polyamide resin or polyvinyl chloride with an inner diameter of 2 to 4 mm and with a length of 0.5 to 2 m.

The vibration imparting device 22 is connected to the ablation catheter with a balloon 1A via the three-way stopcock 8 and the pressure-resistant extension tube 29.

The vibration imparting device is preferably a device that can repeat the suction and the ejection of the liquid for heating 1 to 5 times per second from a viewpoint of effectively generating eddy current in the interior of the balloon 2 and uniforming the surface temperature of the balloon in a short time.

The device that can repeat the suction and the ejection of the liquid for heating 1 to 5 times per second is preferably a device having a pump selected from the group consisting of a roller pump, a diaphragm pump, a bellows pump, a vane pump, a centrifugal pump, and a pump constituted by combination of a piston and a cylinder from a viewpoint of the operation efficiency, configuration, and economics.

EXAMPLES

Hereinafter, specific examples of the ablation catheter with a balloon and the ablation catheter system with a balloon according to the present invention will be described with reference to the drawings. It is to be noted that "a length" represents a length in a direction of a long axis.

Example 1

The balloon 2 made of polyurethane having an outer diameter of 25 mm and a film thickness of 40 μm was prepared by a blow molding method with use of Pellethane (manufactured by Dow Chemical Company).

The outer catheter shaft 3 made of polyurethane having an outer diameter of 3.3 mm, an inner diameter of 2.5 mm, and a length of 800 mm was prepared. Also, the inner catheter shaft 4 having an outer diameter of 1.7 mm, an inner diameter of 1.3 mm, and a length of 930 mm was prepared by an extrusion molding method with use of Daiamid (manufactured by Daicel-Evonik Ltd.) and was inserted into the lumen A 5 of the outer catheter shaft 3.

With a position 15 mm distanced in length from the front end of the inner catheter shaft 4 set as a starting point, a copper wire having an outer diameter of 0.4 mm plated with silver was wound in a rear end direction of the inner catheter shaft 4 to form the coiled in-balloon electrode 10 having a length of 15 mm.

A copper wire having an outer diameter of 0.4 mm plated with silver as the in-balloon electrode lead wire 12 was connected to the rear end of the in-balloon electrode 10 and was fixed by soldering.

An extra fine thermocouple copper wire having an outer diameter of 0.1 mm as one in-balloon temperature sensor lead wire 13 and an extra fine thermocouple constantan wire having an outer diameter of 0.1 mm as the other in-balloon temperature sensor lead wire 13 were connected at the front ends and were fixed by soldering, and a Type T thermocouple obtained by the soldering was used as the in-balloon temperature sensor 11. The in-balloon temperature sensor 11 was fixed at the rear end of the in-balloon electrode 10 by adhesive.

The front portion of the balloon 2 was placed at a position 10 mm distanced in length from the front end of the inner catheter shaft 4, and the front side of the balloon 2 was fixed on an outer circumference of the inner catheter shaft 4 by thermal welding while the rear side of the balloon 2 was fixed on an outer circumference of the front portion of the outer catheter shaft 3 by thermal welding.

Figure 8:
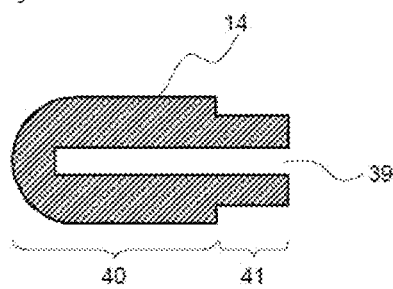
FIG. 8 is a schematic view illustrating a cross-section horizontal to a longitudinal direction of an embodiment of a front portion electrode included in the ablation catheter with a balloon according to the present invention.

A cylindrical column having a length of 7 mm and a diameter of 1.7 mm was prepared with use of platinum, a front end of the cylindrical column is processed in a semispherical shape while a 2-mm part (buried portion 41) in length from a rear end of the cylindrical column to the front side is processed to have a diameter of 1.3 mm, and a hole 39 having a diameter of 0.3 mm and a length of 5 mm was cut from the rear end of the cylindrical column to the front side to prepare the front portion electrode 14 shown in FIG. 8.

The front portion temperature sensor 15 that is a Type T thermocouple prepared from the temperature sensor lead wire 17 in a similar manner to that of the in-balloon temperature sensor 11 was inserted into the hole 39 and was fixed by filling the hole with adhesive.

A copper wire having an outer diameter of 0.4 mm plated with silver as the front portion electrode lead wire 16 was connected to an end section of the buried portion 41 and was fixed by soldering.

The in-balloon electrode lead wire 12, the in-balloon temperature sensor lead wire 13, the front portion electrode lead wire 16, and the front portion temperature sensor lead wire 17 were respectively coated with TEFLON (registered trademark) resins and were inserted into the lumen B 19 of the inner catheter shaft 4.

Figure 9:
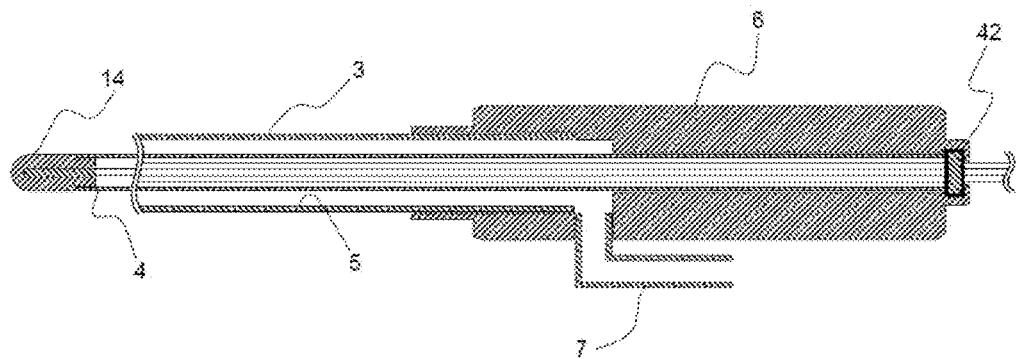
FIG. 9 is a schematic view illustrating a cross-section horizontal to a longitudinal direction of the ablation catheter with a balloon according to the first embodiment of the present invention.

As shown in FIG. 9, the buried portion 41 of the front portion electrode 14 was thrust into the front portion of the inner catheter shaft 4 and was fixed by adhesive so that a 5-mm part in length from the front end of the front portion electrode 14, that is, an exposed portion 40, might be exposed. In this case, the distance from the end section on the front side in the longitudinal direction of the inner catheter shaft 4 to the front end of the front portion electrode 14 in the longitudinal direction is 5 mm.

After the other ends of the in-balloon electrode lead wire 12, the in-balloon temperature sensor lead wire 13, the front portion electrode lead wire 16, and the front portion temperature sensor lead wire 17 inserted into the lumen B 19 of the inner catheter shaft 4 were made to pass through a sealing member 42, the rear portions of the outer catheter shaft 3 and the inner catheter shaft 4 were inserted into the interior of the handle 6 made of polyethylene and were fixed by adhesive to prepare the ablation catheter with a balloon 1A.

The in-balloon electrode lead wire 12, the in-balloon temperature sensor lead wire 13, the front portion electrode lead wire 16, and the front portion temperature sensor lead wire 17 passing through the sealing member 42 were connected to terminals of the circuit switching switch 23A as shown in 4 and were fixed by soldering.

The circuit switching switch 23A and the radio-frequency generator 21 with 1.8 MHz were connected via the radio-frequency current lead wire 26 using a coated copper wire having an outer diameter of 0.5 mm. Also, the circuit switching switch 23A and the temperature control unit in the radio-frequency generator 21 were connected via a pair of temperature measuring signal transmitting lead wires 27 using a coated copper wire having an outer diameter of 0.5 mm and a coated constantan wire having an outer diameter of 0.5 mm. Further, the counter electrode 28 (model number 354; manufactured by ValleyLab) and the radio-frequency generator 21 were connected via a lead wire.

To the side port 7 of the handle 6 was attached the three-way stopcock 8, to which the syringe 9 and the pressure-resistant extension tube 29 that is a tube made of polyvinyl chloride having a length of 1 m, an inner diameter of 2 mm, and an outer diameter of 4 mm were respectively connected. To the other end of the pressure-resistant extension tube 29 was connected via a connecting connector 35 the vibration imparting device 22 rotated 3 times per second, that is, the vibration imparting device 22 repeating suction and ejection of the liquid for heating 3 times per second, and the ablation catheter system with a balloon 20A according to an embodiment of the present invention (hereinafter referred to as EXAMPLE 1 catheter system) was completed.

Example 2

The ablation catheter with a balloon 1B was prepared in the following manner with use of the balloon 2, the outer catheter shaft 3, the inner catheter shaft 4, the in-balloon temperature sensor 11, the front portion electrode 14, and the front portion temperature sensor 15 prepared in similar manners to those in EXAMPLE 1.

With a position 3 mm distanced in length from the front end of the inner catheter shaft 4 set as a starting point, a copper wire having an outer diameter of 0.4 mm plated with silver was wound in a rear end direction of the inner catheter shaft 4 to form the coiled additional in-balloon electrode 37 having a length of 7 mm.

A copper wire having an outer diameter of 0.4 mm plated with silver as the additional in-balloon electrode lead wire 38 was connected to the rear end of the additional in-balloon electrode 37 and was fixed by soldering.

Also, with a position 5 mm distanced in length from the rear end of the additional in-balloon electrode 37 set as a starting point, a copper wire having an outer diameter of 0.4 mm plated with silver was wound in a rear end direction of the inner catheter shaft 4 to form the coiled in-balloon electrode 10 having a length of 7 mm.

A copper wire having an outer diameter of 0.4 mm plated with silver as the in-balloon electrode lead wire 12 was connected to the rear end of the in-balloon electrode 10 and was fixed by soldering.

The balloon 2, the in-balloon temperature sensor 11, the front portion electrode 14, and the front portion temperature sensor 15 were fixed in similar manners to those in EXAMPLE 1, and the in-balloon electrode lead wire 12, the additional in-balloon electrode lead wire 38, the in-balloon temperature sensor lead wire 13, the front portion electrode lead wire 16, and the front portion temperature sensor lead wire 17 were respectively coated with TEFLON (registered trademark) resins and were inserted into the lumen B 19 of the inner catheter shaft 4.

After the other ends of the in-balloon electrode lead wire 12, the additional in-balloon electrode lead wire 38, the in-balloon temperature sensor lead wire 13, the front portion electrode lead wire 16, and the front portion temperature sensor lead wire 17 inserted into the lumen B 19 of the inner catheter shaft 4 were made to pass through the sealing member 42, the rear portions of the outer catheter shaft 3 and the inner catheter shaft 4 were inserted into the interior of the handle 6 made of polyethylene and were fixed by adhesive to prepare the ablation catheter with a balloon 1B.

The in-balloon electrode lead wire 12, the additional in-balloon electrode lead wire 38, the in-balloon temperature sensor lead wire 13, the front portion electrode lead wire 16, and the front portion temperature sensor lead wire 17 passing through the sealing member 42 were connected to terminals of the circuit switching switch 23B as shown in 6 and were fixed by soldering.

To the side port 7 of the handle 6 was attached the three-way stopcock 8, to which the pressure-resistant extension tube 29 was connected. To the other end of the pressure-resistant extension tube 29 was connected via the connecting connector 35 the vibration imparting device 22, and the ablation catheter system with a balloon 20B according to an embodiment of the present invention (hereinafter referred to as EXAMPLE 2 catheter system) was completed.

Comparative Example 1

An ablation catheter system with a balloon (hereinafter referred to as COMPARATIVE EXAMPLE 1 catheter system) was completed in a similar manner to that in EXAMPLE 1 except for preparing a front portion electrode by processing and cutting a cylindrical column having a length of 5 mm, that is, except for causing the distance from the end section on the front side in the longitudinal direction of the inner catheter shaft 4 to the front end of the front portion electrode 14 in the longitudinal direction to be 3 mm.

Comparative Example 2

An ablation catheter system with a balloon (hereinafter referred to as COMPARATIVE EXAMPLE 2 catheter system) was completed in a similar manner to that in EXAMPLE 2 except for preparing a front portion electrode by processing and cutting a cylindrical column having a length of 5 mm, that is, except for causing the distance from the end section on the front side in the longitudinal direction of the inner catheter shaft 4 to the front end of the front portion electrode 14 in the longitudinal direction to be 3 mm.

(Preparation of Ablation Catheter System with Balloon)

A mixed solution at a volume ratio between a contrast medium (HEXABRIX (registered trademark); manufactured by Guerbet KK) and saline of 1:1 was supplied from the syringe 9 as the liquid for heating, air inside the interior of the balloon 2 and the lumen A 5 was removed, and then the balloon 2 was inflated so that the maximum diameter thereof might be 25 mm.

Subsequently, the three-way stopcock 8 was switched to remove air inside the pressure-resistant extension tube 29, and the three-way stopcock 8 was further switched to make the vibration imparting device 22 and the lumen A 5 communicate with each other.

(Measurement of Ablation Temperatures)

Figure 10:
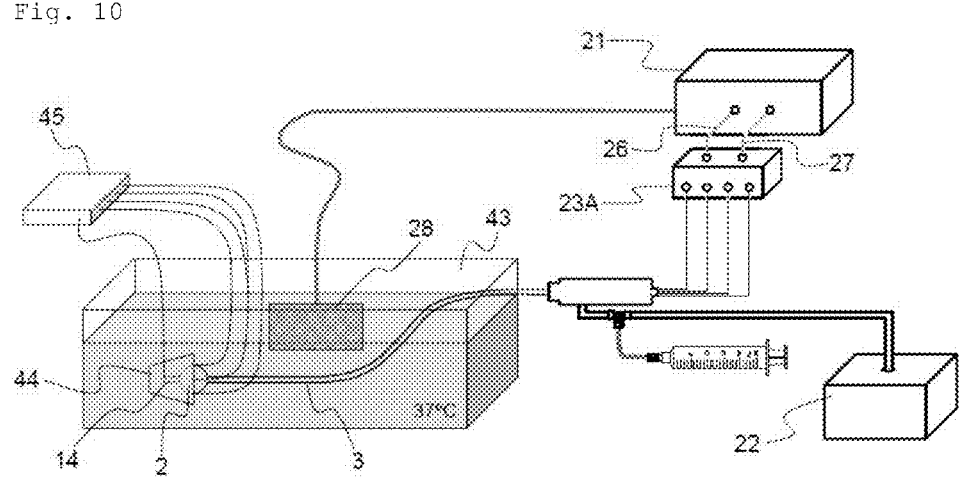
FIG. 10 is a schematic view of an experimental system for ablation temperatures.

FIG. 10 shows an experimental system to measure a spot ablation temperature and a balloon ablation temperature of each of the prepared ablation catheter systems with a balloon. A water tank 43 to the inner wall of which the counter electrode 28 was attached was filled with 35 L saline, and the temperature of the saline was kept at 37° C.

A pseudo myocardial tissue 44 made of polyacrylamide into a shape in which the balloon 2 inflated so that the maximum diameter thereof might be 25 mm would be fit was prepared in a transparent container and installed in the water tank 43.

After the balloon 2 was immersed into the saline in the water tank 43 and was fit into the pseudo myocardial tissue 44, temperature sensors A to D were arranged at four locations in a circumferential direction of the balloon 2 at equal intervals, a temperature sensor E was further arranged on the surface of the front portion electrode 14, and the temperature sensors were respectively connected to a temperature recording meter 45.

After the circuit switching switch 23A or 23B was switched to the balloon heating circuit 25A or 25B, the radio-frequency generator 21 and the vibration imparting device 22 were operated simultaneously, the balloon 2 was heated at a setting temperature of 70° C., and the temperatures of the surfaces of the balloon 2 that the temperature sensors A to D contacted and the temperature of the surface of the front portion electrode 14 that the temperature sensor E contacted were respectively measured 120 seconds after the beginning of heating by the temperature recording meter 45. The result is shown in Table 1.

After the liquid for heating was removed from the interior of the balloon 2, and the circuit switching switch 23A or 23B was switched to the front end heating circuit 24A or 24B, the radio-frequency generator 21 was operated, the front portion electrode was heated at a setting temperature of 60° C., and the temperature of the surface of the front portion electrode 14 that the temperature sensor E contacted was measured 30 seconds after the beginning of heating by the temperature recording meter 45. The result is shown in Table 2.

TABLE 1

| Catheter system | Measurement temperature of each temperature sensor [° C.] | | | | |
|---|---|---|---|---|---|
| | A | B | C | D | E |
| EXAMPLE 1 | 61 | 60 | 59 | 61 | 39 |
| EXAMPLE 2 | 58 | 58 | 57 | 58 | 39 |
| COMPARATIVE EXAMPLE 1 | 61 | 61 | 60 | 61 | 59 |
| COMPARATIVE EXAMPLE 2 | 59 | 58 | 58 | 58 | 39 |

TABLE 2

| Catheter system | Measurement temperature of temperature sensor E [° C.] |
|---|---|
| EXAMPLE 1 | 60 |
| EXAMPLE 2 | 60 |
| COMPARATIVE EXAMPLE 1 | 60 |
| COMPARATIVE EXAMPLE 2 | 60 |

As shown in Table 1, in a case where the circuit switching switch 23A or 23B was switched to the balloon heating circuit 25A or 25B, the surface temperatures of the balloon 2 of each of the ablation catheter systems with a balloon, that is, the balloon ablation temperatures were in a range of 50 to 65° C., which were preferable temperatures for ablation of a myocardial tissue. However, the surface temperature of the front portion electrode of each of the ablation catheter systems with a balloon, that is, the spot ablation temperature, increased to the extent that a myocardial tissue contacting the front portion electrode was undesirably ablated only in the case of the COMPARATIVE EXAMPLE 1 catheter system.

It is estimated that the reason for the increase in the surface temperature of the front portion electrode of the COMPARATIVE EXAMPLE 1 catheter system is excessive concentration of radio-frequency currents caused by the insufficient length of the exposed portion of the front portion electrode, that is, the insufficient distance from the end section on the front side in the longitudinal direction of the inner catheter shaft 4 to the front end of the front portion electrode in the longitudinal direction.

On the other hand, as for the COMPARATIVE EXAMPLE 2 catheter system, the surface temperature did not increase although the distance from the end section on the front side in the longitudinal direction of the inner catheter shaft 4 to the front end of the front portion electrode in the longitudinal direction is equal to that of the COMPARATIVE EXAMPLE 1 catheter system. This is considered to be because arranging the two in-balloon electrodes made radio-frequency currents flow only in the interior of the balloon 2 and did not make the radio-frequency currents flow in the front portion electrode 14.

As is apparent from the result in Table 1, to prevent an unintended surface temperature increase in the front portion electrode, the distance from the end section on the front side in the longitudinal direction of the inner catheter shaft 4 to the front end of the front portion electrode in the longitudinal direction needs to be 4 mm or longer, or two in-balloon electrodes need to be arranged to make radio-frequency currents flow only in the interior of the balloon 2.

As shown in Table 2, in a case where the circuit switching switch 23A or 23B was switched to the front end heating circuit 24A or 24B, the surface temperature of the front portion electrode of each of the ablation catheter systems with a balloon, that is, the spot ablation temperature, was controlled to a setting temperature in a range of 50 to 65° C., which were preferable temperatures for ablation of a myocardial tissue.

The present invention can be used as an ablation catheter with a balloon and an ablation catheter system with a balloon for treatment of arrhythmias such as an atrial fibrillation, endometriosis, cancer cells, hypertension, and the like.

DESCRIPTION OF REFERENCE SIGNS 1A, 1B . . . ablation catheter with a balloon, 2 . . . balloon, 3 . . . outer catheter shaft, 4 . . . inner catheter shaft, 5 . . . lumen A, 6 . . . handle, 7 . . . side port, 8 . . . three-way stopcock, 9 . . . syringe, 10 . . . in-balloon electrode, 11 . . . in-balloon temperature sensor, 12 . . . in-balloon electrode lead wire, 13 . . . in-balloon temperature sensor lead wire, 14 . . . front portion electrode, 15 . . . front portion temperature sensor, 16 . . . front portion electrode lead wire, 17 . . . front portion temperature sensor lead wire, 19 . . . lumen B, 20A, 20B . . . ablation catheter system with a balloon, 21 . . . radio-frequency generator, 22 . . . vibration imparting device, 23A, 23B . . . circuit switching switch, 24A, 24B . . . front end heating circuit, 25A, 25B . . . balloon heating circuit, 26 . . . radio-frequency current lead wire, 27 . . . temperature measuring signal transmitting lead wire, 28 . . . counter electrode, 29 . . . pressure-resistant extension tube, 30 . . . roller, 31 . . . rotating shaft, 32 . . . guide surface, 33 . . . elastic tube, 34 . . . reservoir portion, 35 . . . connecting connector, 36 . . . sealing connector, 37 . . . additional in-balloon electrode, 38 . . . additional in-balloon electrode lead wire, 39 . . . hole, 40 . . . exposed portion, 41 . . . buried portion, 42 . . . sealing member, 43 . . . water tank, 44 . . . pseudo myocardial tissue, 45 . . . temperature recording meter.

The invention claimed is:

1. An ablation catheter system, comprising:
    an ablation catheter including
        a catheter shaft;
        a balloon fixed to a distal end section of the catheter shaft in a longitudinal direction of the catheter shaft;
        a lumen communicating with the balloon from a proximal section of the catheter shaft in the longitudinal direction;
        an in-balloon electrode and an in-balloon temperature sensor arranged in an interior of the balloon; and
        a front portion electrode and a front portion temperature sensor extending distally from the distal end section of the catheter shaft in the longitudinal direction; and
    a counter electrode arranged outside the balloon;
    a radio frequency generator;
    a first balloon heating circuit using the radio frequency generator for operation with the counter electrode and the in-balloon electrode, and using the balloon temperature sensor to control the radio frequency generator;
    a front end heating circuit using the radio frequency generator for operation with the counter electrode and the front portion electrode, and using the front portion temperature sensor to control the radio frequency generator; and
    a circuit switch for switching between the first balloon heating circuit and the front end heating circuit,
    wherein the front portion electrode has an exposed portion that is 4 to 10 mm in the longitudinal direction.

2. The ablation catheter system according to claim 1, further comprising an impedance measuring device measuring Impedance of the first balloon heating circuit or the front end heating circuit.

3. The ablation catheter system according to claim 1, wherein the ablation catheter has a second in-balloon electrode which is arranged in the interior of the balloon.

4. The ablation catheter system according to claim 3, further comprising:
    a second balloon heating circuit using the radio frequency generator for operation with the in-balloon electrode and the second in-balloon electrode, and using the balloon temperature sensor to control the radio frequency generator;
    wherein the circuit switch switches between the front end heating circuit and the second balloon heating circuit.

5. The ablation catheter system according to claim 3, wherein:
    the radio-frequency generator generates radio-frequency currents that flow between the in-balloon electrode and the counter electrode and between the in-balloon electrode and the second in-balloon electrode or between the front portion electrode and the counter electrode; and
    the ablation catheter system further comprises a vibration Imparting device imparting a vibration to a liquid for heating by periodically repeating suction and ejection of the liquid for heating from the lumen.

6. The ablation catheter system according to claim 5, wherein the vibration imparting device includes a pump selected from the group consisting of a roller pump, a diaphragm pump, a bellows pump, a vane pump, a centrifugal pump, and a pump including a piston and a cylinder.

* * * * *